US008066859B2

(12) United States Patent
Johnston et al.

(10) Patent No.: US 8,066,859 B2
(45) Date of Patent: Nov. 29, 2011

(54) ELECTROCHEMICAL CARBON MONOXIDE SENSOR SUPERVISION

(75) Inventors: Derek Johnston, Aurora, IL (US); Gene Brooks, Montgomery, IL (US)

(73) Assignee: BRK Brands, Inc., Aurora, IL (US)

( * ) Notice: Subject to any disclaimer, the term of this patent is extended or adjusted under 35 U.S.C. 154(b) by 524 days.

(21) Appl. No.: 12/258,552

(22) Filed: Oct. 27, 2008

(65) Prior Publication Data

US 2009/0107838 A1   Apr. 30, 2009

Related U.S. Application Data

(60) Provisional application No. 60/982,503, filed on Oct. 25, 2007.

(51) Int. Cl.
*G01N 27/26* (2006.01)

(52) U.S. Cl. ........ 204/406; 204/424; 205/782; 205/784; 205/784.5; 205/785.5; 340/632; 340/693.6

(58) Field of Classification Search .................. 204/406, 204/424; 205/782, 784, 784.5, 785.5; 340/438, 340/506, 635, 636.1, 636.12, 636.13, 636.15, 340/632, 693.6
See application file for complete search history.

(56) References Cited

U.S. PATENT DOCUMENTS

| 5,517,182 | A | | 5/1996 | Yasunaga | |
|---|---|---|---|---|---|
| 5,694,118 | A | | 12/1997 | Park | |
| 5,886,638 | A | | 3/1999 | Tanguay | |
| 5,912,626 | A | * | 6/1999 | Soderlund | 340/693.5 |
| 5,969,600 | A | * | 10/1999 | Tanguay | 340/438 |
| 6,452,510 | B1 | * | 9/2002 | Zysko | 340/970 |
| 6,819,252 | B2 | | 11/2004 | Johnston | |

* cited by examiner

*Primary Examiner* — Bruce Bell
(74) *Attorney, Agent, or Firm* — Lawrence J. Shurupoff

(57) ABSTRACT

A sensor supervision system for periodically providing a test to accesses the status of a gas detection sensor, such as a carbon monoxide (CO) sensor, is provided. To access the status of the CO sensor, a processor provides a voltage to the sensor supervision system, such that a voltage is applied to CO sensor, charging the CO sensor. The status of the CO sensor is accessed by determining the change in the voltage charge of the CO sensor between two sampling time points. If the first sample voltage is substantially equal to the second sample voltage, i.e., a substantially constant voltage, the carbon monoxide sensor fails the test. However, if there is an change is the voltage change between the first and second sampled time points, the CO sensor passes the test.

6 Claims, 5 Drawing Sheets

ELECTROCHEMICAL CARBON MONOXIDE SENSOR SUPERVISION

CROSS-REFERENCE TO RELATED APPLICATION

The present invention claims priority to U.S. Provisional Application No. 60/982,503 for ELECTROCHEMICAL CARBON DIOXIDE SENSOR SUPERVISION, filed on Oct. 25, 2007, the contents of which are herein incorporated by reference in it entirety.

FIELD OF THE INVENTION

The present disclosure relates to a gas detection system, a more particularly to a system and method for testing gas detection sensors.

BACKGROUND OF THE INVENTION

Devices for detecting and generating a warning with respect to dangerous conditions, such as the presence of carbon monoxide (CO), are known. For example, various devices and systems are described in U.S. Pat. Nos. 5,517,182 to Yasunaga, issued on May, 14, 1996; 5,694,118 to Park et al., issued Dec. 2, 1997, 5,886,639 to Tanguay, issued Mar. 23, 1999, and 6,819,256 to Johnston et al., issued Nov. 16, 2004, the contents of all which are expressly incorporated by reference in their entirety.

In general, CO detectors employ one of three types of detectors: semiconductor, biomimetic and electrochemical."

Semiconductor CO sensors typically employ a thin layer of metal, such as tin dioxide, maintained at a relatively high temperature (e.g., 100.degree. C. to 400.degree. C.). The surface conductivity of the metal varies generally proportionally in accordance with exposure to ambient CO concentration. The semiconductor chip measures the migration of oxygen molecules through the surface of the sensor material.

Biomimetic sensors utilize a transparent substrate disk coated with a synthetic hemoglobin that mimics the reaction of natural hemoglobin in the presence of carbon monoxide. The biomimetic material darkens with cumulative absorption of CO. A light emitting diode (LED) transmits light through the biomimetic material to a photosensitive device. When the material becomes sufficiently dark to prevent adequate light from reaching the photosensitive device, the detector sounds an alarm.

Electrochemical sensors, in general, employ a chemical reaction to convert CO to carbon dioxide ($CO_2$) to create a chemical imbalance in a portion of the cell which in turn generates a current indicative of the amount of CO present. Some electrochemical sensors utilize two chambers (one for CO and one for hydrogen).

SUMMARY OF THE INVENTION

The present disclosure provides a system and method for testing a gas detection sensor. The gas detection sensor can be provided in a gas detection unit having a sensor supervision system for accessing a status of the gas detection sensor. The gas detection unit can be a carbon monoxide (CO) detector, or a combination smoke/CO detector.

The gas detection sensor can be a carbon monoxide sensor, where the sensor supervision system periodically accesses the status of the CO sensor. To access the status of the CO sensor, a processor in the gas detection unit provides a voltage to the sensor supervision system, such that a voltage is applied to the CO sensor. During the testing, the CO sensor is charged like a capacitor.

The status of the CO sensor is accessed by determining the change in the voltage charge of the CO sensor between two sampling time points. If the first sample voltage is substantially equal to the second sample voltage the carbon monoxide sensor fails the test, and is bad. If the first sample voltage is not equal to the second sample voltage the carbon monoxide sensor passes the test, and is good.

BRIEF DESCRIPTION OF THE DRAWINGS

A more complete understanding of the present invention, and the attendant advantages and features thereof, will be more readily understood by reference to the following detailed description when considered in conjunction with the accompanying drawings wherein.

DETAILED DESCRIPTION OF THE INVENTION

Figure 1:
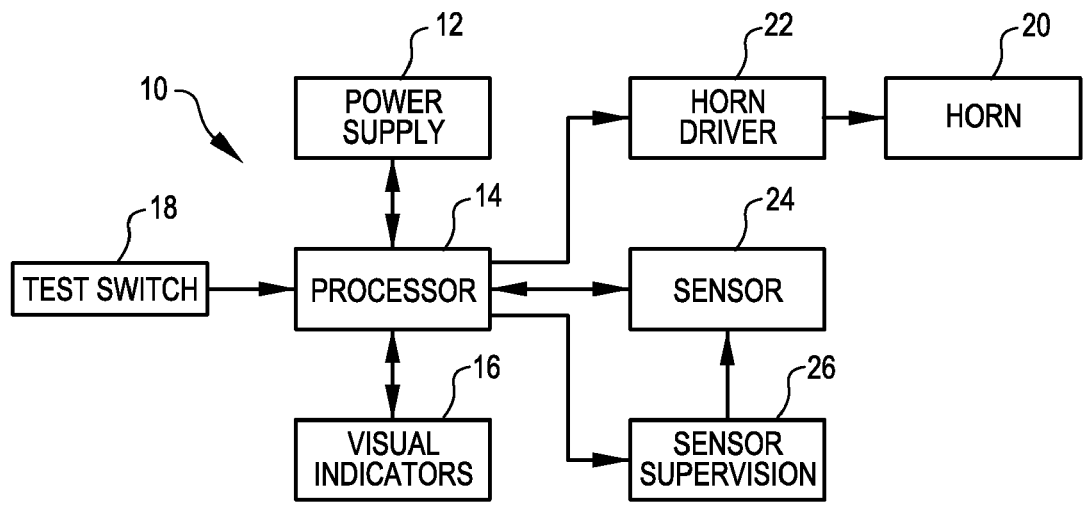
FIG. 1 is a block diagram for a gas detection unit is accordance with the present disclosure.

Referring to FIG. 1, an exemplary detector unit 10 is provided. The detector unit 10 can be, for example, a carbon monoxide (CO) detector or a combination smoke/CO detector. The detector unit 10 includes: a power supply 12; a processor 14; visual indicators 16; a manually actuatable test/reset switch 18; a suitable audio transducer (e.g., piezoelectric horn 20) and cooperating horn driver 22; at least one suitable sensor 24; and a sensor supervision system 26. The at least one sensor 24 can be a CO sensor, or can further include a smoke sensor.

The power supply 12 may be any supply capable of providing the necessary voltage levels for the various components of the system. In circumstances where AC line voltage is available, power supply 12 suitably includes a suitable AC-DC converter. The power supply may further include a battery back-up. Alternatively, power supply 12 may employ a battery as the primary power source.

Figure 2:
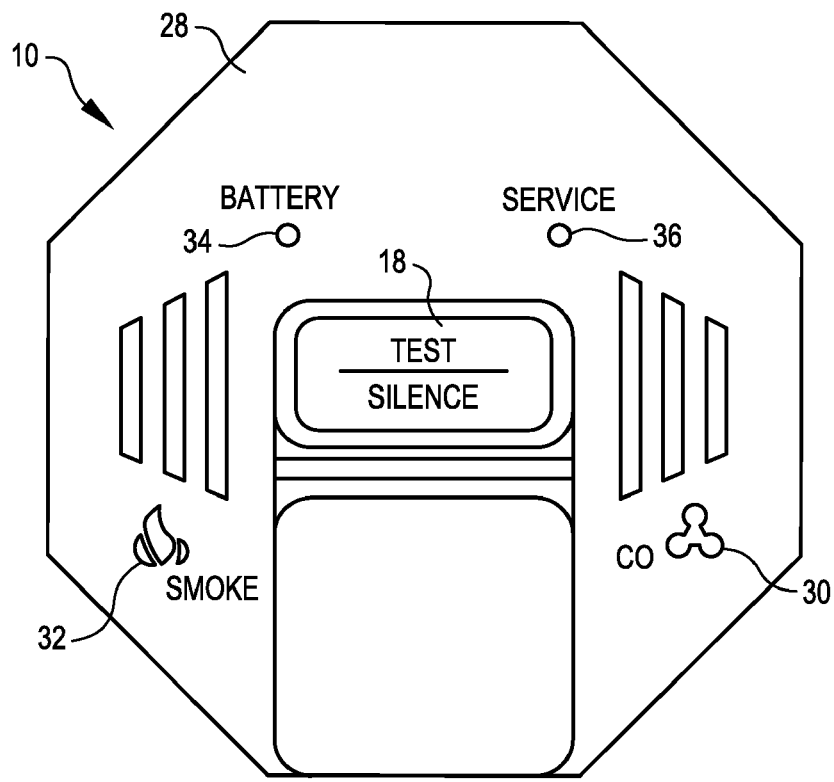
FIG. 2 depicts a plan view of an exemplary gas detection unit of the present disclosure.

FIG. 2 depicts a front plan view of an exemplary housing of a combination smoke/CO detector unit 10. The housing 28 includes a CO alarm indicator 30, a smoke alarm indicator 32, a low battery indicator 34, and a service status visual indicator 36. The housing 30 also preferably includes a single test/silence button 18.

With respect to FIGS. 1 and 2, the processor 14 can include an internal clock, Read Only Memory (ROM), Random Access Memory (RAM), and a plurality of input/output (I/O) pins. The processor 14 controls the overall operation of the detector unit 10 and processes information to determine a hazardous condition of carbon monoxide or smoke in the atmosphere. It will be understood that a variety of processing units or processors could be used without departing from the spirit and scope of the present invention.

Figure 3:
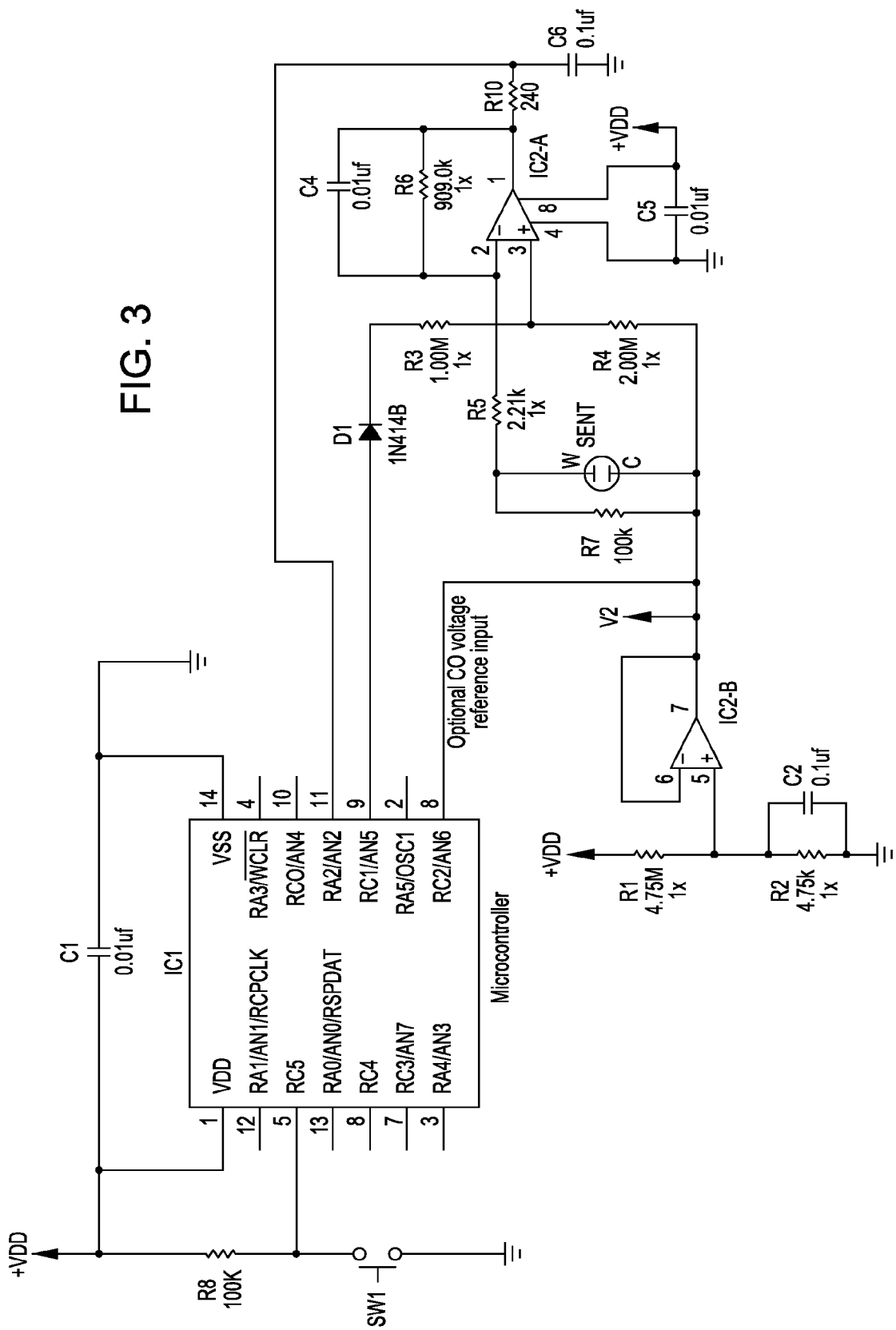
FIG. 3 depicts a circuit diagram for an electrochemical CO sensor supervision circuit of the present disclosure.

Referring to FIG. 3, a circuit diagram of an electrochemical CO sensor supervision is provided. The sensor supervision circuitry 40 includes resistors R1-7, a capacitors C1, C2, C5, C5, and C6, a diode switch D1, and an electrochemical CO sensor SEN 1. The CO sensor SEN 1 of the CO detection circuitry 40 is utilized to detect the presence or absence of carbon monoxide in the surrounding atmosphere.

The CO sensor SEN 1 is diagnosed for an open or short condition periodically. The sensor diagnostic can occur automatically at predetermined time intervals, or manually by the depression of the test button 18. The sensor diagnostic occurs when the processor 14 switches a small current through the sensor supervision circuitry 40. A current in created by means of a voltage potential applied to the anode of the diode switch D1 for a predetermined time interval. This voltage is placed across resistors R3 and R4 forming a voltage divider from VDD to the offset voltage reference V2 (V2 offset voltage reference is derived by IC2b configured as a voltage buffer and resistors R1 and R2 connected from VDD to ground.)

The voltage developed across R4 is placed on the positive input of IC2a. This same potential is also developed on the negative input of IC2a and is placed across the resistor R5 and the CO sensor SEN 1 with respect to the reference supply V2, thus providing a series current though these two parts.

The CO sensor SEN 1 under test looks like a large capacitor to the circuit and because of the series current through the CO sensor SEN 1, the CO sensor SEN 1 begins to charge. As the charge voltage across the CO sensor SEN 1 starts to increase the voltage across the series resistor R5 begins to decrease. This decrease in voltage across R5 also decreases the current in the series loop with respect to the offset voltage V2.

As the current through R5 decreases these is a proportional change in the feedback current of R6. Therefore, as the feedback resistor current through R6 and IC2a (current-to-voltage converter circuit) decreases so will its current output. The output voltage of IC2a is sampled by the processor's 14 analog-to-digital converter at two different time points. The two samplings are compared to each other and a decision is made to pass or fail the CO sensor SEN 1.

Figure 4:
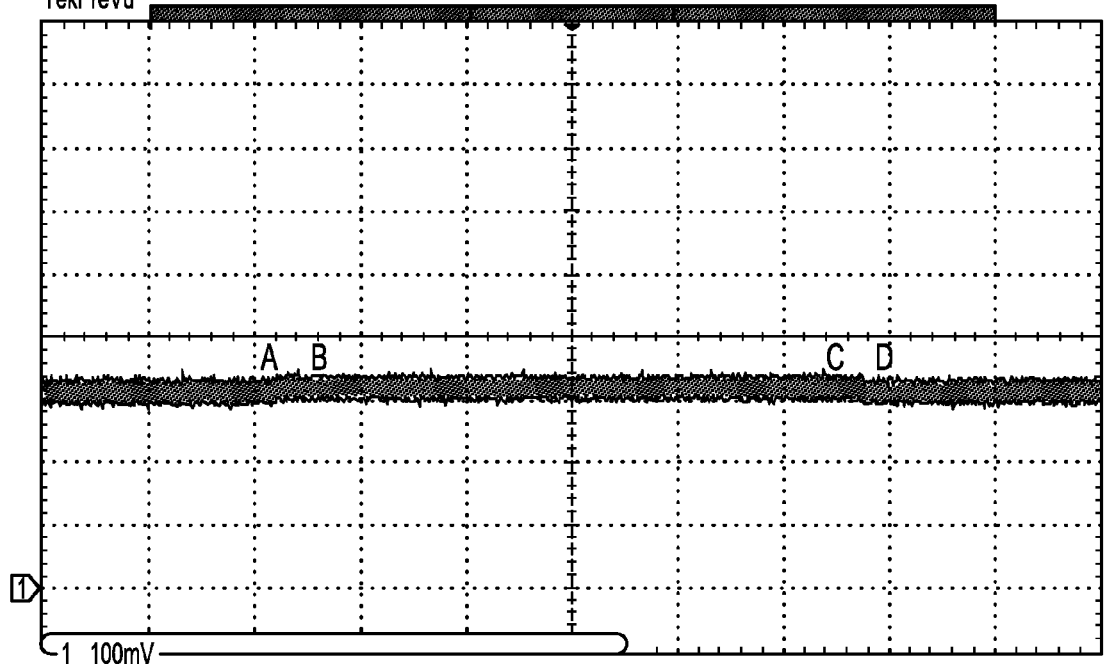
FIG. 4 depicts a graphic representation of an electrochemical CO sensor in an open condition.

If the CO sensor SEN 1 is open the voltage between the sampling time points is a low constant and the CO sensor SEN 1 fails (See FIG. 4). If the CO sensor SEN 1 is shorted the voltage between the sampling time points is a high constant and the CO sensor SEN 1 fails (See FIG. 5). If the CO sensor SEN 1 is good the voltage between the sampling time points will decrease (See FIG. 6).

Figure 6:
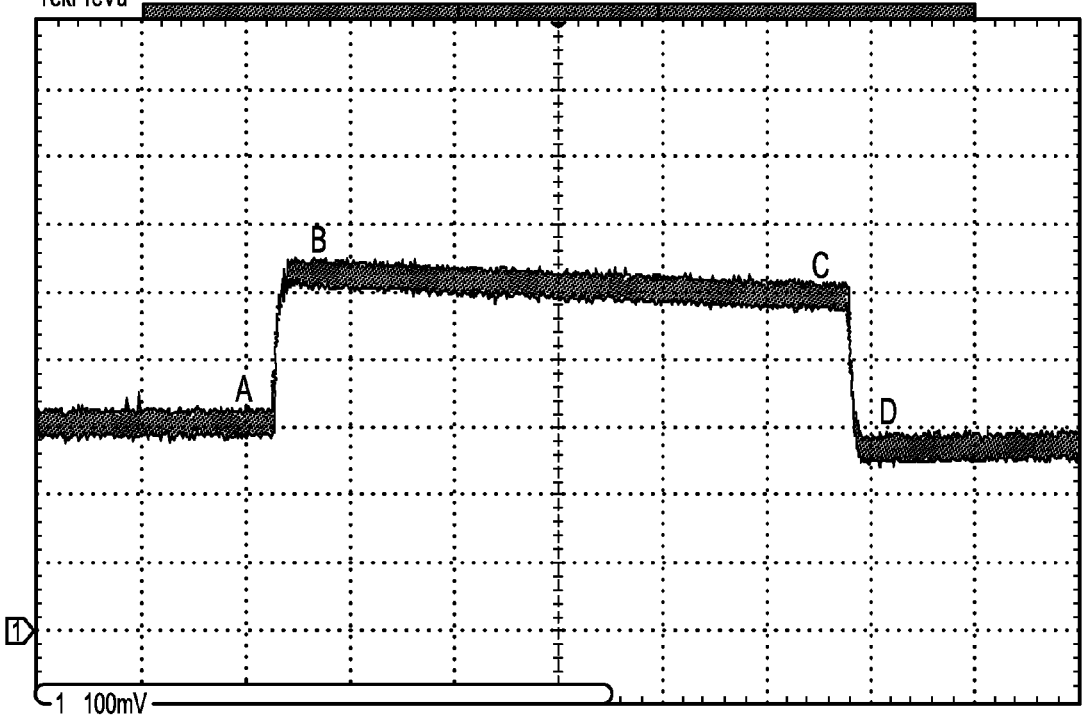
FIG. 6 depicts a graphic representation of an electrochemical CO sensor in a normal condition.
Figure 7:
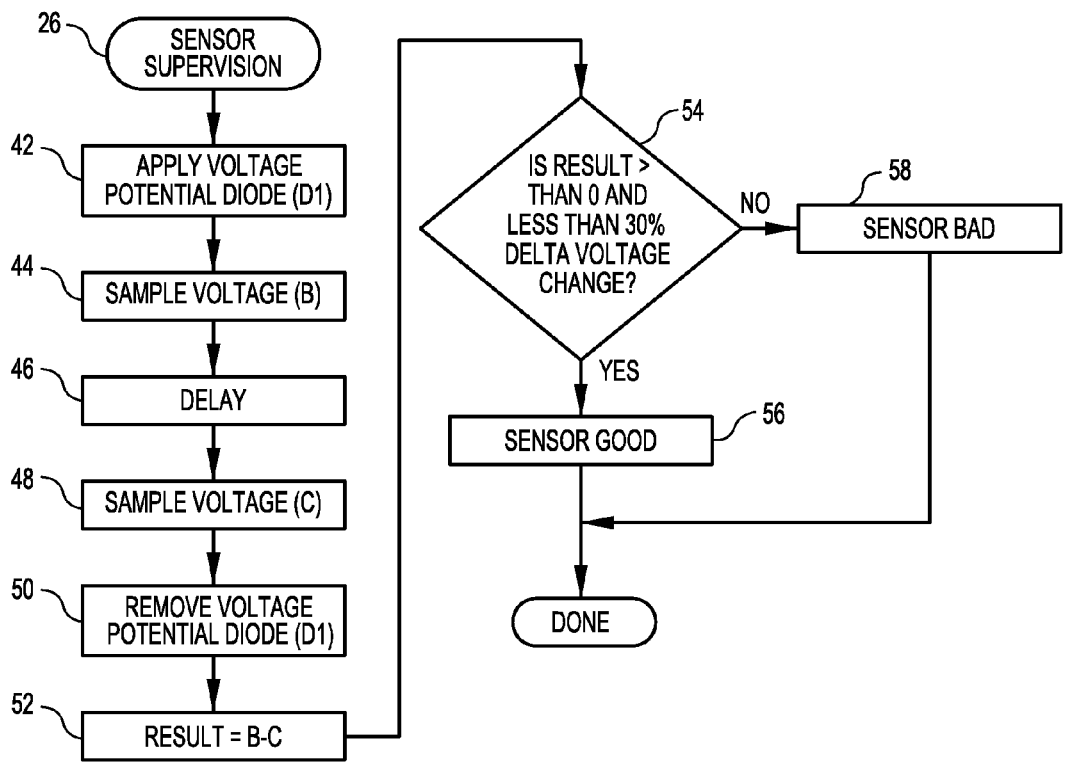
FIG. 7 depicts a first diagnostic method for testing an electrochemical CO sensor.

Referring to FIG. 7, an exemplary method for testing the CO sensor SEN 1 is provided. A voltage potential is applied to diode D1 42. The voltage $V_B$ is sampled at a time point B 44. A time delay is provided between sample time point B and a second sample at time point C 46. After the time delay, the voltage $V_C$ is sampled at time point C 48. The voltage potential is removed from the diode D1 50. The delta voltage ($\Delta V$) is calculated by subtracting the sampled voltage at sample time point B from the voltage at sample time point C 52, $V_B-V_C$. The $\Delta V$ is then checked 54, if the $\Delta V$ is greater then zero then the sensor passes, is good 56. As an additionally verification, if there is less then a 30% percent voltage drop between the time points B and C then CO sensor is good 56. This condition is depicted in FIG. 6, which shows a decrease is voltage between time points B and C.

Figure 5:
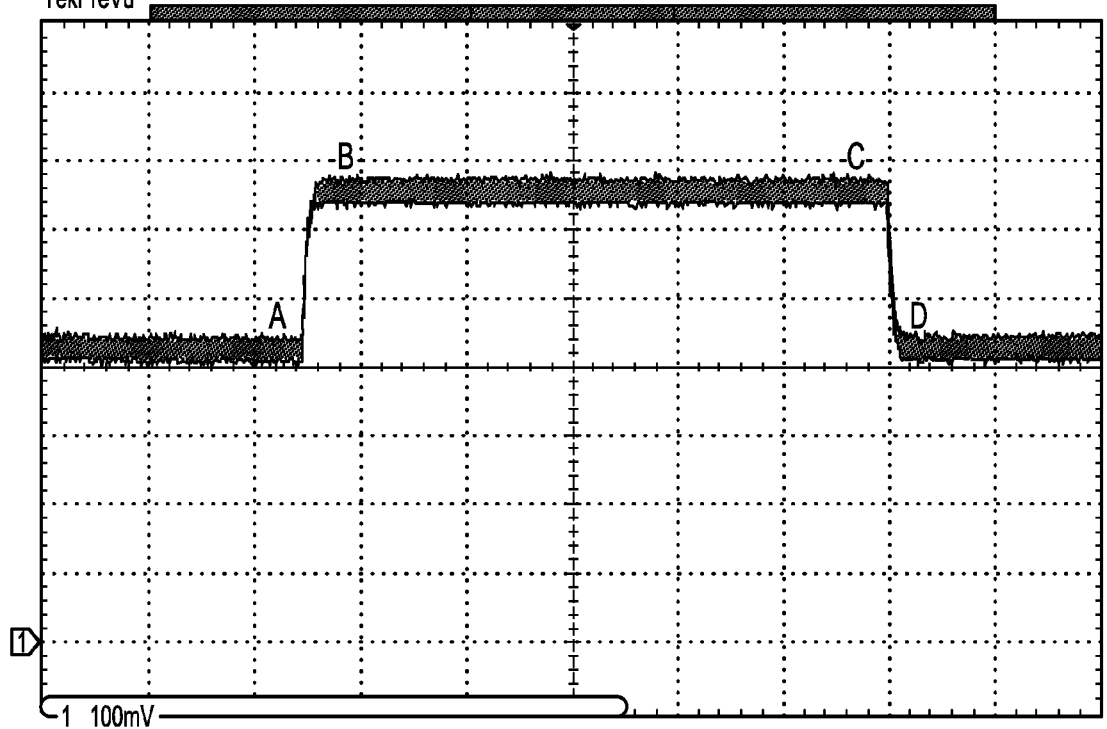
FIG. 5 depicts a graphic representation of an electrochemical CO sensor in a shorted condition.

However, if the $\Delta V$ is substantially equal to zero then the sensor fails, is bad 58, and open or short condition exist in the CO sensor. As noted above, the differentiation between an open and a short condition is that the short condition has a higher constant voltage between time points B and C then does the open condition. As an additionally verification, if there is greater then a 30% percent voltage drop between the time points B and C then CO sensor may be bad 58. This condition is depicted in FIGS. 4 and 5, between time point B and C.

After the sensor diagnostic test, the status of the sensor can be provided by a visual or audible indicator. For example, the visual indicator 16 can flash a green light for a passing of the diagnostic test, a good CO sensor, or a red light for a failing of the diagnostic test, a bad Co sensor.

Alternatively, a suitable audio transducer 20 can provide a first sound for a passing of the diagnostic test, a good CO sensor, or a second sound for a failing of the diagnostic test, a bad test, where the first and second sounds are different. For example, a passing of the diagnostic test can be provided by a single chirp from the audio transducer 20, and a failing of the diagnostic test can be followed by a plurality of chirps from the audio transducer 20.

Figure 8:
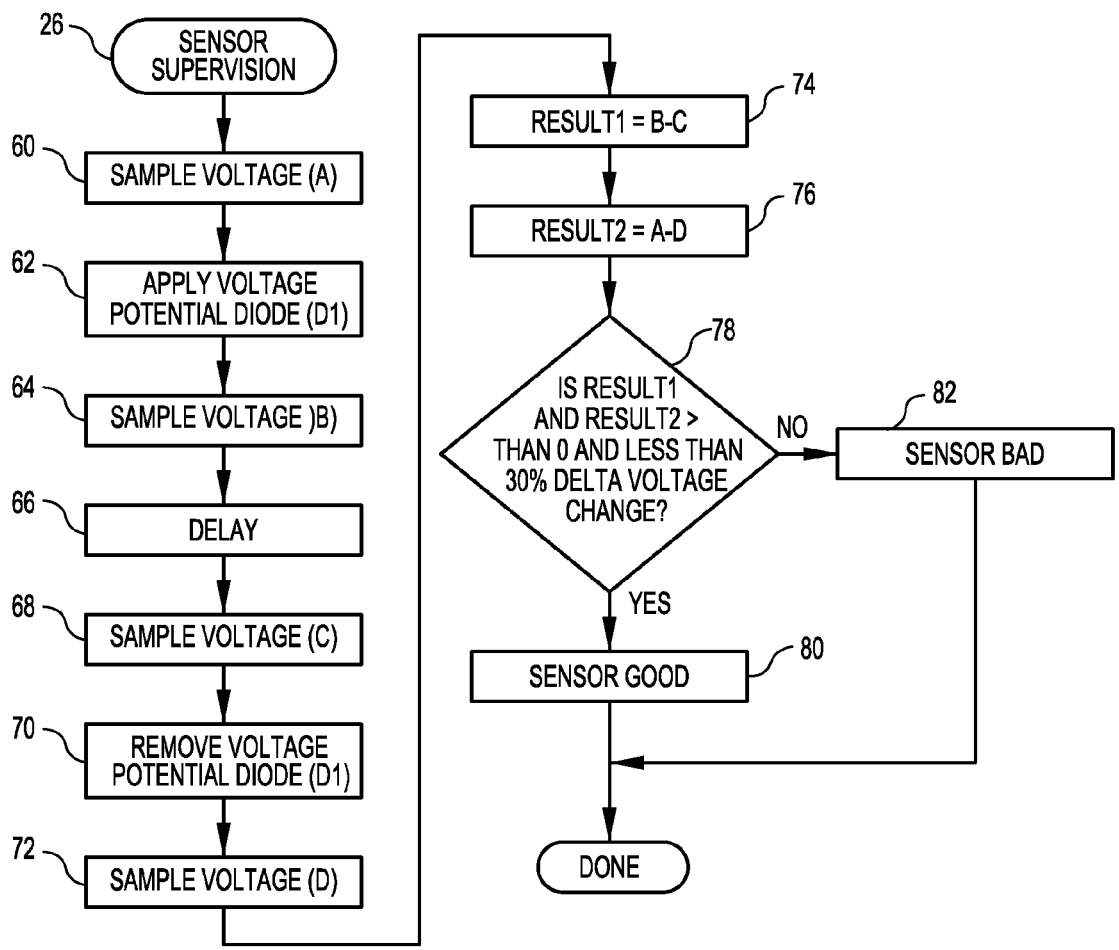
FIG. 8 depicts a second diagnostic method for testing an electrochemical CO sensor.

Referring to FIG. 8, an alternative testing method can be provided were two or more pairs of time sampling points are utilized. A voltage $V_A$ sample is taken at time point A 60. A voltage potential is applied to diode D1 62. The voltage $V_B$ is samples at a time point B 64. A time delay is provided between sample time point B and sample time point C 66. After the time delay 66, the voltage $V_c$ is sampled at time point C 68. The voltage potential is removed from the diode D1 70. A sample voltage $V_D$ is taken at time point D 72. The delta voltage ($\Delta V1$) is calculated by subtracting the sampled voltage at sample time point B from the voltage at sample time point C 72, $V_B-V_C$. The delta voltage ($\Delta V2$) is calculated by subtracting the sampled voltage at sample time point A from the voltage and sample time point D 76, $V_A-V_D$. The voltage differences $\Delta V1$ and $\Delta V2$ are checked 74. If $\Delta V1$ and $\Delta V2$ are greater then zero then the sensor passes, is good 80. As an additionally verification, if there is less then a 30% percent voltage drop between the time points B and C and between A and d then CO sensor is good 80.

However, if the voltage differences $\Delta V1$ and $\Delta V2$ are substantially equal to zero then the sensor fails, is bad 80, i.e., and an open or short condition exists in the CO sensor. As an additionally verification, if there is greater then a 30% percent voltage drop between the time points B and C and between time points A and D, then CO sensor may be bad 82.

In the above examples, to calculate the voltage difference $\Delta V$ the voltage at a second sample time point was subtracted from the voltage at a first sample time point, i.e., $V_B-V_C$ or $V_A-V_D$. However, it is understood that the status of the CO sensor is based on where or not the is a change in the voltage between the sampling time point. As such, the voltage difference $\Delta V$ can be calculated by subtracting the voltage at a first sample time point from the voltage at a second sample time point, i.e., $V_C-V_B$ or $V_D-V_A$.

In this manner, a passing sensor can be based on whether or not the voltage difference is greater or less than zero. If the voltage differences is substantially equal to zero, i.e., a substantially constant voltage, then the sensor fails, i.e., and open or short condition exists in the CO sensor. If the voltage difference is not equal to zero then the CO sensor passed, is good.

All references cited herein are expressly incorporated by reference in their entirety.

It will be appreciated by persons skilled in the art that the present invention is not limited to what has been particularly shown and described herein above. In addition, unless mention was made above to the contrary, it should be noted that all of the accompanying drawings are not to scale. A variety of modifications and variations are possible in light of the above teachings without departing from the scope and spirit of the invention, which is limited only by the following claims.

What is claimed is:

1. A gas detection unit, comprising:
   a carbon monoxide sensor; and
   a sensor supervision circuit including a means for accessing a status of the carbon monoxide sensor
   a means for providing a voltage charge to the carbon monoxide sensor, and means for reading a change in the voltage charge of the carbon monoxide sensor between a first and second time point.

2. A gas detection unit as set forth in claim 1, wherein when the means for reading a change in the voltage charge of the carbon monoxide sensor between a first and second time point reads a change in the voltage charge between the first and second time points the status of the carbon monoxide sensor is good.

3. A gas detection unit as set forth in claim 2, wherein when the means for reading a change in the voltage charge of the carbon monoxide sensor between a first and second time point reads a substantially constant voltage charge between the first and second time points the status of the carbon monoxide sensor is bad.

4. A gas detection unit as set forth in claim 3, further comprising:
   a processor;
   a power supply;
   a visual indicator; and
   an audio indicator.

5. A gas detection unit as set forth in claim 3, where the carbon monoxide sensor is an electrochemical sensor.

6. A method for determining the status of a carbon monoxide sensor comprising:
   providing a voltage to the carbon monoxide sensor;
   charging the carbon monoxide sensor:
   reading a first sample voltage from the carbon monoxide sensor at a first time point;
   reading a second sample voltage from the carbon monoxide sensor at a second time point, wherein the first time point is different from the second time point;
   determining the status of the carbon monoxide sensor, where when the first sample voltage is equal to the second sample voltage the carbon monoxide sensor is bad and when the first sample voltage is not equal to the second sample voltage the carbon monoxide sensor is good.

* * * * *